United States Patent [19]
Parks

[11] Patent Number: 5,642,737
[45] Date of Patent: Jul. 1, 1997

[54] DEVICE FOR ALLEVIATING SNORING

[76] Inventor: Scotty M. Parks, 7815 McCallum #9103, Dallas, Tex. 75252

[21] Appl. No.: 643,743

[22] Filed: May 6, 1996

[51] Int. Cl.$^6$ .................................................. A61F 5/56
[52] U.S. Cl. ................................. 128/848; 128/859
[58] Field of Search ..................... 128/848, 859–862; 433/6, 24, 42, 44, 46; 2/2

[56] References Cited

U.S. PATENT DOCUMENTS

| | | |
|---|---|---|
| 2,696,668 | 12/1954 | Fox . |
| 4,003,132 | 1/1977 | Beck . |
| 5,211,559 | 5/1993 | Hart et al. . |
| 5,234,005 | 8/1993 | Kittelsen ..................... 128/859 |
| 5,277,202 | 1/1994 | Hays . |
| 5,289,829 | 3/1994 | Roehrig . |
| 5,313,960 | 5/1994 | Tomasi . |
| 5,365,945 | 11/1994 | Halstrom . |
| 5,409,017 | 4/1995 | Lowe . |
| 5,427,117 | 6/1995 | Thornton ..................... 128/859 |
| 5,462,066 | 10/1995 | Snyder . |
| 5,467,783 | 11/1995 | Meade ..................... 128/848 |
| 5,499,633 | 3/1996 | Fenton . |

OTHER PUBLICATIONS

"Self–Adhering Nylon Tape"; Journal of AMA; vol. 168 No. 7; Oct. 19, 1958, p. 900.

*Primary Examiner*—Michael A. Brown
*Attorney, Agent, or Firm*—Drude Faulconer

[57] ABSTRACT

An anti-snore device for alleviating snoring which includes an upper member and a lower member which can be molded to fit over a wearer's dental contours (i.e. upper and lower teeth) similarly as do athletic mouthguards. A simple latching means comprised of hook tape is provided which allows a wearer to easily and quickly adjust the members to a proper position to alleviate snoring and then latch the members in said position while the wearer sleeps.

7 Claims, 2 Drawing Sheets

DEVICE FOR ALLEVIATING SNORING

DESCRIPTION

1. Technical Field

The present invention relates to an device for alleviating snoring and in one of its aspects relates to an oral anti-snore device to be worn within the mouth of a person while sleeping to hold the lower jaw of the wearer forward of the upper jaw during sleep to alleviate snoring.

2. Background Art

Snoring and the more serious "sleep apnea" are problems with which almost everyone is familiar. These problems are normally caused, at least in part, by the partial obstruction or narrowing of the airway in a person's throat when he or she reclines. It has been found that these problems can be substantially alleviated in that the airway of most people can be maintained in a substantially open position even when reclining by moving the mandible (lower jaw) forward relative to the maxilla ( upper jaw) and then holding the jaws in this position while the person sleeps.

A wide variety of "anti-snore" devices have been proposed to accomplish this objective. One such group is comprised of devices which have (a) an upper member and a lower member which conform respectively to the upper and lower dental impressions or contours (i.e. teeth and gums) of the wearer and (b) a means for positioning and holding the lower member forward with respect to the upper member when both are in the mouth of the wearer. The upper and lower members typically consist of acrylic or elastomeric plates or the like which can be custom-fitted by a professional (e.g. similar to orthodontic retainers) or which can be bought over-the-counter and then self-molded by the wearer to fit his/her mouth (e.g. similar to commercially-available mouthguards used by athletes).

In order for these devices to be accepted by potential wearers, they must be able not only to alleviate snoring but they must also be comfortable enough to allow the wearer to sleep normally. To do this, a universal device (i.e. one size that can be used by a wide range of people) must be able to be adjusted to and latched in several different positions depending on the physical requirements of the particular wearer. Accordingly, the means which is used to hold the members (hence the jaws of the wearer) in the desired position must be adjustable through some range of positions in order for the device to find the universal appeal required to make such an over-the-counter device economical.

Currently, there are several such known "anti-snore" devices, for example see those disclosed in U.S. Pat. Nos. 5,313,960; 5,365,945; 5,409,017; 5,427,117, and 5,499,633 and the various prior art devices cited and discussed therein. Each of these prior art devices have a particular means for adjusting and/or holding the upper and lower members in a preset position to allow the device to be fitted to an individual wearer. However, the latching means used in these devices provides only for the members to be latched in one of a few, preset positions and can not be further adjusted for positions which might lie therebetween which, in turn, may be more comfortable for a particular wearer.

Further, the latching means in these types of prior art devices are generally bulky and cumbersome which, in turn, may cause some discomfort to the wearer. Still further, these prior art latching means are relatively complicated thereby requiring some degree of sophistication in fitting the device to a particular wearer. These features would appear to detract from their market appeal to the general public. Accordingly, it is sincerely believed that there is a need for a relatively simple, universal device which can quickly and easily be adjusted by a wearer to a position most comfortable during sleep, especially where such devices are to be sold over-the-counter to the general public.

SUMMARY OF THE INVENTION

The present invention provides an anti-snore device, which in its preferred form, can be produced as a universal device which, in turn, can be sold over-the-counter at a reasonable cost. This allows the device to be available to a large number of snorers who otherwise may not be able to afford to obtain relief. The present device, while similar to known prior art devices of this type, includes a simple hook-tape releasable latching means for securing the device in a position wherein the wearer's lower jaw will be comfortably positioned forward relative to the upper jaw thereby alleviating snoring. The ease with which the hook tape latching means can be engaged and disengaged provides an easy way for the wearer to adjust the device to the most comfortable position for that particular wearer.

More specifically, the present invention provides an anti-snore device for alleviating snoring which is comprised of an upper member and a lower member which when inserted into a wearer's mouth will fit over the wearer's dental contours, i.e. upper and lower teeth and/or gums, respectively. These members can be cast and fitted by a dental professional or preferably, can be constructed similarly to those used as athletic mouthguards. That is, the members can be self-formed and fitted by the wearer without the need of a dental professional.

The upper and lower members and are comprised of shells which may be constructed of dental material used for appliances of this type, e.g. methylmethacrylate. The shells have a basic U-shaped cross-section which define a trough which, in turn, is filled with a deformable material, an ethylene-vinyl acetate copolymer resin. The members are heated, e.g. submerged in hot water, to soften the deformable material and then positioned within the wearer's mouth who bites down to impress his/her particular dental contours into the softened material. The members are cooled to allow the deformable material to set.

In the present invention, a simple releasable latching means is provided which allows a wearer to easily and quickly adjust the members to a proper position to alleviate snoring and then hold the members in said position while the wearer sleeps. The latching means is simply comprised of a hook tape connector which, in turn, is comprised of two cooperating elements, i.e. a hooked element and a pile element. One of the elements is attached to the lower front of the upper member while the other element is attached to the upper front of the lower member. As is well known, when the hooks of the first element is pressed downwardly into the loops of the second element, the two lock together and can only be separated by firmly pulling them away from each other.

When the device is ready for use, the upper and lower members are inserted into the wearer's mouth where they fit over the upper and lower dental arches, respectively. The mouth is held slightly open so that the hook-tape elements are not engaged thereby allowing the wearer to move his/her lower jaw forward with respect to the upper jaw. When the lower jaw is in a forward but comfortable position with relation to the upper jaw, the wearer closes his/her mouth and presses the hook-tape elements together to secure and latch the upper and lower members in the desired position.

The hook tape connector provides an infinite number of possible relative positions between the members whereby the wearer is not bound by preset positions normally present in the known prior art devices of this type.

BRIEF DESCRIPTION OF THE DRAWINGS

The actual construction, operation, and apparent advantages of the present invention will be better understood by referring to the drawings which are not necessarily to scale and in which like numerals identify like parts, and in which.

BEST KNOWN MODE FOR CARRYING OUT THE INVENTION

Figure 1:
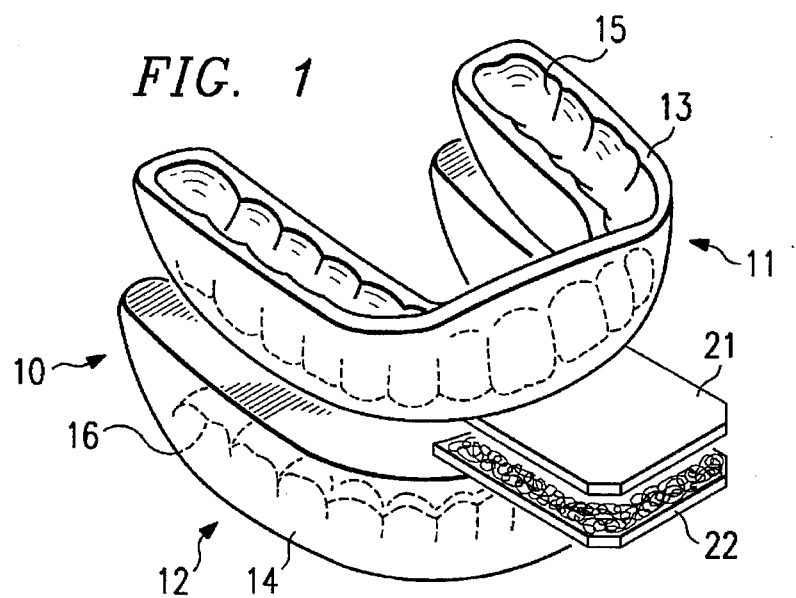
FIG. 1 is a perspective view of the anti-snore device of the present invention.
Figure 2:
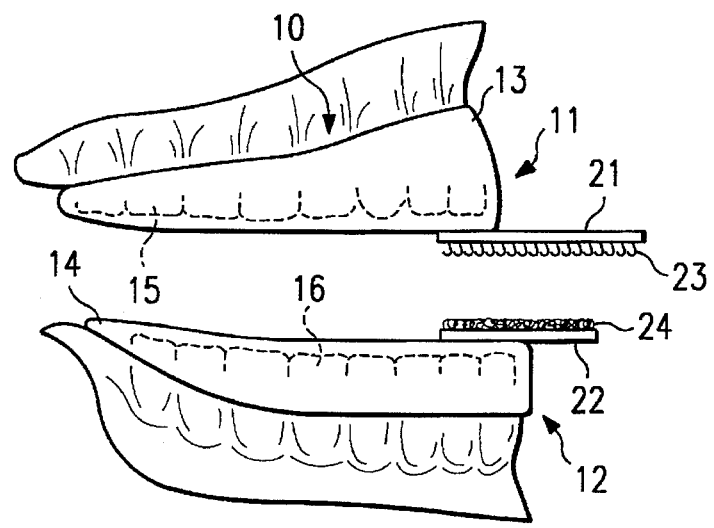
FIG. 2 is side view of the device of FIG. 1.
Figure 3:
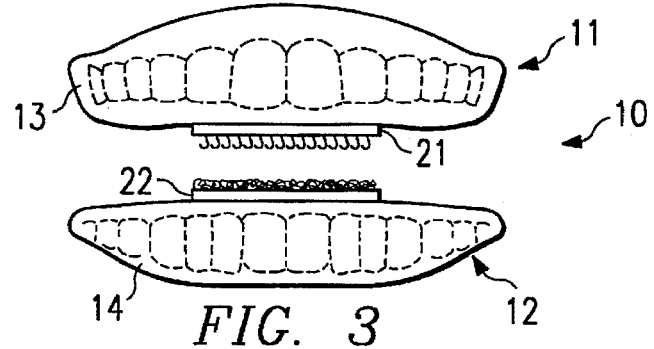
FIG. 3 is a front view of the device of FIG. 1.
Figure 4:
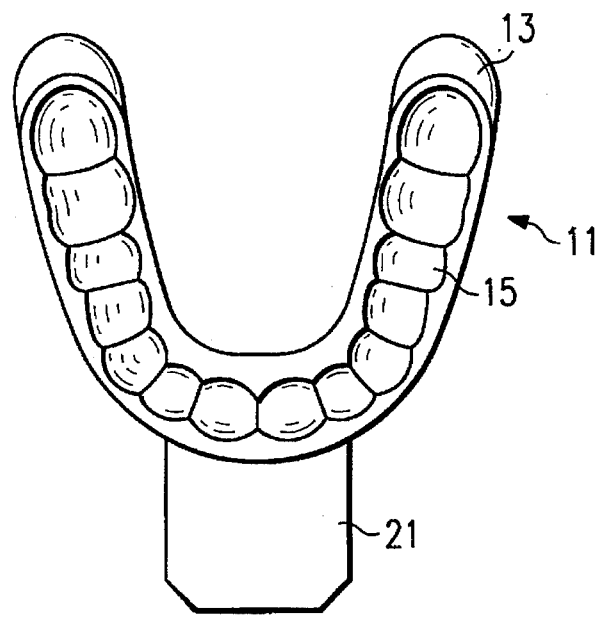
FIG. 4 is a top view of the device of FIG. 1.

Referring more particularly to the drawings, FIGS. 1–4, the anti-snore device 10 for alleviating snoring in accordance with the present invention. Device 10 is comprised of an upper member 11 and a lower member 12. As will be understood, upper member 11 is adapted to be shaped so that when it is inserted into a wearer's mouth, it will conform to and fit over the upper dental contour (i.e. teeth and/or gums) of the wearer. Likewise, the lower member 12 is adapted to conform to and fit over the lower contour of the wearer. It will be recognized that both members 11 and 12 can be cast or molded and fitted by a dental professional using commonly known techniques to provide permanant-type plates, similar to dentures, orthodontic retainers, etc..

Preferably, however, in the present invention, both members 11 and 12 are constructed similarly as are athletic mouthguards in that the members can be self-formed and fitted by the wearer without the need for assistance from a dental professional. This allows a single universal device (may require more than one size, e.g. large, small, mens', womens', etc.) to be marketed over-the-counter where the majority of snorers can seek relief at minimum expense without embarrassment or undue inconvenience.

More specifically, both members 11 and 12 are comprised of shells 13, 14, respectively, which are constructed of any material suitable and approved for dental use, e.g. methyl-methacrylate or a polycarbonate resin thermoplastic such as "LEXAN", commercially-available from General Electric Company. The shells of device 10 are molded to have a basic configuration similar to denture plates or the like and are of dimensions which are common to and will fit within the mouths of a wide group of people (e.g. adult males, etc.). Each shell has a U-shaped cross-section which defines a trough which, in turn, is adapted to receive the upper and lower dental arches when positioned within the mouth of the wearer.

The respective troughs in each shells 13 and 14 are filled with a deformable material 15, 16, respectively. Material 15, 16 is bonded within its respective trough and, as will be fully understood in the art, allows each individual wearer to custom, self-fit device 10 to his/her own particular dental contours without requiring the assistance of a dental professional.

The deformable material can be any material used in other deformable, self-molding dental devices such as athletic mouthguards and the like. One such well known material used for this purpose is an ethylene-vinyl acetate copolymer resin; e.g. "ELVAX", commercially available from DuPont Company. Another such material is a resin sold under the trademark "CLEARFLEX", commercially available from Vernon-Benshoff Co.. The upper and lower members 11, 12 can be submerged in hot water or otherwise heated to a temperature (e.g. 150° F.) at which the deformable material will soften. Once the deformable material is softened, the members can then be positioned within the mouth of the particular individual wearer who bites down to impress his/her particular dental contours into the softened material. The members are removed and allowed to cool to room temperature to set the deformable material to conform with the desired contours of the wearer.

It will be realized that the device as described up to this point is similar to other known devices of this basic type, e.g. see U.S. Pat. Nos. 5,313,960; 5,427,117; 5,409,017; and 5,499,633. However, in the present invention, a novel latching means 20 is provided which allows a wearer to easily and quickly adjust members 11 and 12 to a position necessary to alleviate snoring and then hold the members in said position while the wearer sleeps.

More specifically, means 20 is comprised of a hook tape connector which, in turn, is comprised of an upper support 21 which is attached to the front lower side of upper member 11 and a lower support 22 which is attached to the upper front of lower member 12. As will be seen from the drawings, supports 21, 22 are positioned so that they will align substantially vertically with each other and will be substantially horizontally parallel when members 11 and 12 are within the mouth of a wearer. Each support can be formed of any material which is approved for dental applications, e.g. thin, elongated tabs of semi-rigid, flexible plastic-like material, e.g. "LEXAN".

Each support carries one of the two cooperating elements which form the well known fastener which is commonly known as "hook tape", e.g. commercially-available "VELCRO". Such tape is comprised of a first male or hooked element 23 which is made up of a large number of microscopic hooks and a second female or pile element 24 which is made up of a similarly large number of microscopic loops. While hooked element 23 is shown as being carried on the lower side of support 21 on upper member 11 and looped element 24 as being carried on the upper side of support 22 on lower member 12, these positions of the respective elements can be reversed without affecting the present invention in any way since in either position, the hook tape will operate in the same manner.

As is well known, when the hooks of the first element is pressed relatively straight-downwardly into the loops of the second element, the two become locked together. This connection between the elements resist separation when the elements are moved laterally or horizontally with respect to each other and can only be easily separated when they are firmed pulled relatively-vertically away from each other.

Elements 23 and 24 can be glued or otherwise secured to their respective supports or may be integrally formed onto the support as is the case with some commercially-available hook tapes, e.g. that used in "3-M Marine Reclosable Attachment System", commercially-available from the 3-M Company. Once in place, the opposing elements of the hook tape will be align and opposed from each other so that they will engage when members 11 and 12 are moved towards each other.

In operation, the deformable material 21, 22 in members 11 and 12, respectively, are self-molded to conform to the wearer's dental contours as described above. When the wearer is ready to go to sleep, he/she inserts the members into his/her mouth so that the upper member 11 fits over the upper teeth and the lower member 12 fits over the lower teeth. The mouth is held slightly open so that the hook-tape elements 23, 24 on members 11, 12, respectively, are not in engagement thereby allowing the wearer to freely move his/her lower jaw forward with respect to the upper jaw.

When the lower jaw is in a forward but comfortable position with relation to the upper jaw, the wearer closes his/her mouth and presses the hook-tape elements together to secure upper member to the lower member thereby locking the wearer's jaws in said position. The wearer can now enjoy a good night's sleep without disturbing others by excessive snoring.

It can be seen that due to the nature of hook-tape connecting means 20, the lower jaw of a wearer can be positioned at an almost infinite number of relative positions with respect to the upper jaw (i.e. at extremely small increments) so that the just right position for a particular wearer to be obtained. This can be done quickly and easily by the wearer without the need of a professional. The proper relative positioning of the jaws is not limited to only a few preset positions as is the case with the prior art devices. Further, the latching means 20 can be easily released and readjusted at will if a setting proves uncomfortable. That is, the wearer is not bound or limited to any preset positions which, in turn, may not provide for the most comfortable position for a particular wearer. The present invention allows a wearer to experiment with various positions until one is found that is most comfortable for the wearer.

Figure 5:
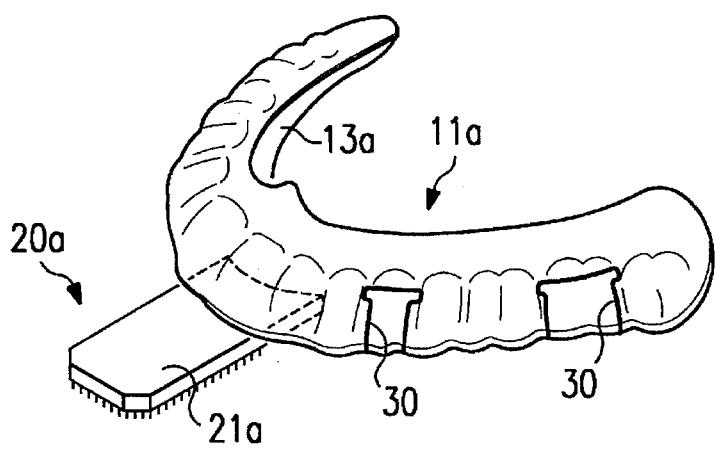
FIG. 5 is an exploded, perspective view of another embodiment of the device in accordance with the present invention.
Figure 5:
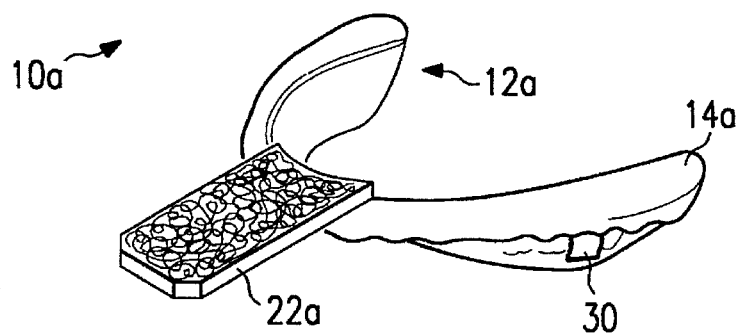

FIG. 5 illustrates another embodiment of the present invention of the type where upper member 11a and lower member 12a of anti-snore device 10a are molded by a dental professional. In this embodiment, no deformable material is required. Members 11a and 12a are made from any suitable material commonly used for dental appliances of this type, e.g. methylmethacrylate. As the shells 13a and 14a are molded to fit the dental contours of a particular wearer, clasps, e.g. C-clasps, ball clasps, or U-clasps 30 (only U-clasps shown) are embedded in the material to aid in holding the respective members in place. Such clasps could also be used in the previously described modification if desired.

Latching means 20a is basically the same as means 20 described above. That is, means 20a is comprised of a hook-tape connector which, in turn, is comprised of an upper support 21a attached to upper member 11a and a lower support 22a attached to member 12a. One element of the hook tape is carried by the upper support 21a and the other element of the hook tape is carried by the lower support 22a. The operation of this embodiment is the same as described above in relation to device 10.

What is claimed is:

1. An anti-snore device for alleviating snoring of a wearer comprising:

an upper member adapted to positioned within the mouth of said wearer and over the upper dental contour of said wearer;

a lower member adapted to positioned within the mouth of said wearer and over the lower dental contour of said wearer; and a latching means for securing said upper member to said lower member in a position wherein said lower member is forward with respect to said upper member, said means comprising:

hook tape comprised of two elements, a hook element and a pile element, one of said two elements carried by one of said members and the other of said two elements carried by the other of said members.

2. The anti-snore device of claim 1 wherein said upper and lower members include:

deformable material which when softened can conform to the respective dental contours of said wearer.

3. The anti-snore device of claim 1 wherein said upper and lower members are comprised of a material which is permanently molded by a dental professional to conform to the respective dental contours of said wearer.

4. The anti-snore device of claim 3 wherein said material is methylmethacrylate.

5. The anti-snore device of claim 1 wherein said one element of said hook tape being attached to the lower front of said upper member and said other element of said hook tape being attached to the upper front of said lower member so that said hook tape elements with align and oppose each other when said upper and lower members are in the mouth of said wearer.

6. The anti-snore device of claim 1 wherein said upper member and said lower member respectively comprise:

a shell having a U-shaped cross-section defining a trough;

deformable material in said trough which when softened can conform to the respective dental contours of said wearer.

7. The anti-snore device of claim 6 wherein said deformable material is comprised of a ethylene-vinyl acetate copolymer resin.

* * * * *